United States Patent [19]
Kolts et al.

[11] Patent Number: 4,620,051
[45] Date of Patent: Oct. 28, 1986

[54] DEHYDROGENATION AND CRACKING OF $C_3$ AND $C_4$ HYDROCARBONS TO LESS SATURATED HYDROCARBONS

[75] Inventors: John H. Kolts, Ochelata; Gary A. Delzer, Bartlesville, both of Okla.

[73] Assignee: Philips Petroleum Company, Bartlesville, Okla.

[21] Appl. No.: 758,983

[22] Filed: Jul. 25, 1985

[51] Int. Cl.$^4$ .................................. C07C 5/333
[52] U.S. Cl. ........................... 585/663; 585/651; 585/653; 585/661
[58] Field of Search ............... 585/651, 653, 661, 663

[56] References Cited

U.S. PATENT DOCUMENTS

| | | | |
|---|---|---|---|
| 2,415,477 | 2/1947 | Folkins et al. | 585/651 |
| 3,644,557 | 2/1972 | Senes et al. | 585/651 |
| 3,751,514 | 8/1973 | Hoppstock et al. | 585/653 |
| 3,751,516 | 8/1973 | Frech et al. | 585/653 |
| 3,766,278 | 10/1973 | Bogart et al. | 585/651 |
| 4,087,350 | 5/1978 | Kolombos et al. | 585/653 |
| 4,093,536 | 6/1978 | Heckelsberg | 585/653 |
| 4,152,300 | 5/1979 | Riesser | 502/324 |
| 4,159,970 | 7/1979 | Heckelsberg | 502/324 |
| 4,471,151 | 9/1984 | Kolts | 585/651 |

FOREIGN PATENT DOCUMENTS

| | | | |
|---|---|---|---|
| 47-42703 | 12/1972 | Japan | 585/653 |
| 1306087 | 2/1973 | United Kingdom | 585/651 |
| 0422165 | 8/1974 | U.S.S.R. | 585/651 |
| 0626111 | 9/1978 | U.S.S.R. | 585/651 |

Primary Examiner—John Doll
Assistant Examiner—Lance Johnson
Attorney, Agent, or Firm—C. F. Steininger

[57] ABSTRACT

A method of selectively cracking $C_3$ and $C_4$ hydrocarbons to $C_2$ hydrocarbons, particularly ethylene, in which a body of cracking catalyst is established in a reaction zone and the feed hydrocarbons are passed through the body of catalyst while maintaining the conditions sufficient to convert the feed hydrocarbons to product hydrocarbons, including, a temperature in the upstream end of the body of catalyst at least about 100° C. below the temperature in the downstream end of the body of catalyst. The cracking catalyst is preferably selected from the group consisting of: at least one oxide of manganese and at least one oxide of magnesium; at least one oxide of manganese and at least one oxide of at least one metal selected from the group consisting of Lanthanum Series metals, preferably lanthanum or cerium, and niobium; at least one oxide of iron and at least one oxide of magnesium; and at least one oxide of iron and at least one oxide of a Lanthanum Series metals or niobium. The active life of the catalyst, for the selective conversion to $C_2$ hydrocarbons and particularly ethylene, is extended by adding promoting amounts of oxides of calcium, strontium, barium, tin or antimony or oxides of silicon, aluminum or titanium or chromium to certain of the basic catalysts. Manganese may also be added to the catalysts containing iron oxide. The addition of steam, during the conduct of the process, also extends the active life of the catalyst and may, optionally, be utilized with the catalysts free of oxides of iron and is essential to operation with catalysts containing oxides of iron.

40 Claims, No Drawings

DEHYDROGENATION AND CRACKING OF $C_3$ AND $C_4$ HYDROCARBONS TO LESS SATURATED HYDROCARBONS

The present invention relates to the conversion of $C_3$ and $C_4$ hydrocarbons to less saturated hydrocarbons, in the presence of a cracking catalyst. In a more specific aspect, the present invention relates to a method for the conversion of $C_3$ and $C_4$ alkanes to less saturated hydrocarbons, particularly ethylene and propylene and preferably ethylene, in the presence of a cracking catalyst.

BACKGROUND OF THE INVENTION

Olefins, such as ethylene and propylene, have become major feedstocks in the organic chemical and petrochemical industries. Of these, ethylene is by far the most important chemical feedstock since the requirements for ethylene feedstocks are about double those for propylene feedstocks. Consequently, improved methods for the conversion of less valuable hydrocarbons to ethylene and propylene, and particularly to ethylene, are highly desirable.

Numerous suggestions have been made for the production of ethylene and propylene, particularly ethylene, from various feedstocks by a wide variety of processes.

At the present time, ethylene is produced almost exclusively by dehydrogenation or thermal cracking of ethane and propane, naptha and, in some instances, gas oils. About 75% of the ethylene currently produced in the United States is produced by steam cracking of higher normally gaseous hydrocarbon components of natural gas, since natural gas contains from about 5 volume % to about 60 volume % of hydrocarbons other than methane. However, in most instances, the content of ethane and higher normally gaseous hydrocarbons in natural gas is less than about 25% and usually less than about 15%. Consequently, these limited quantities of feedstocks, which are available for the production of ethylene and propylene and particularly ethylene, must be utilized efficiently. Unfortunately, these processes result in low conversions to olefins, and selectivity to ethylene, as opposed to propylene, is poor. In addition, relatively severe conditions, particularly temperatures in excess of about 1000° C., are required and such processes are highly energy intensive.

In order to reduce the severity of the conditions and, more importantly, to improve the conversion of normally gaseous feedstocks, to ethylene and propylene, and the selectivity to ethylene, numerous processes involving the use of solid contact materials have been proposed. Some of these proposals utilize inert solid contact materials to improve contact between the feed hydrocarbons and steam and also to maintain a more even temperature throughout the zone of reaction. In other instances, the solid contact material is catalytic in nature. Such use of solid contact materials, particularly catalysts, have resulted in modest improvements in conversion to ethylene and propylene but the selectivity to ethylene is improved very little. It is, therefore, highly desirable that improved catalytic processes be developed, particularly processes which increase the selectivity to ethylene, as opposed to propylene. However, little is understood concerning the manner in which such catalysts function, why certain components are effective while similar components are ineffective or why certain combinations of components are effective and other combinations are not. Obviously, a number of theories have been proposed by workers in the art, but this only adds to the confusion, since it appears that each theory explains why a particular catalytic material works well but does not explain why similar catalytic materials do not work and why other dissimilar materials are effective. As a result, the art of catalytic conversion of hydrocarbons to olefins remains highly unpredictable.

SUMMARY OF THE INVENTION

It is therefore an object of the present invention to provide an improved method for the conversion of $C_3$ and $C_4$ feed hydrocarbons to less saturated hydrocarbons, which overcomes the above and other disadvantages of the prior art. Still another object of the present invention is to provide an improved method for the catalytic conversion of $C_3$ and $C_4$ hydrocarbons to less saturated hydrocarbons, particularly ethylene and propylene. Yet another object of the present invention is to provide an improved method for the conversion of $C_3$ and $C_4$ hydrocarbons to ethylene and propylene, in which the selectivity to ethylene is significantly improved. These and other objects of the present invention will be apparent from the following description.

In accordance with the present invention, feed hydrocarbons comprising at least one of $C_3$ and $C_4$ hydrocarbons are converted to less saturated product hydrocarbons, with a high selectivity to $C_2$ hydrocarbons and particularly ethylene, by establishing a body of cracking catalyst in a reaction zone, introducing the feed hydrocarbons into the upstream end of the body of catalyst, passing the feed through the body of catalyst in contact with the catalyst, withdrawing product hydrocarbons from the downstream end of the body of catalyst and maintaining conditions within the reaction zone sufficient to convert the feed hydrocarbons to the product hydrocarbons, including a temperature in the upstream end of the body of catalyst which is at least about 100° C. below the temperature in the downstream end of the body of catalyst. Cracking catalysts which are particularly effective in the process, due to their ability to selectively produce $C_2$ hydrocarbons and particularly ethylene, include:

(a) a catalyst comprising at least one oxide of manganese and at least one oxide of magnesium;

(b) a catalyst comprising at least one oxide of manganese and at least one oxide of at least one metal selected from the group consisting of Lanthanum Series metals, particularly lanthanum and cerium, and niobium;

(c) a catalyst comprising at least one oxide of iron and at least one oxide of magnesium; and (d) a catalyst comprising at least one oxide of iron and at least one oxide of at least one metal selected from the group consisting of Lanthanum Series metals and niobium.

The selectivity and active life of these catalysts, before regeneration is desirable, are also improved by certain metal oxide promoters. The active life of the catalyst is also improved by carrying out the process in the presence of steam, particularly when the catalyst contains an oxide of iron. The effectiveness of the catalyst is also improved by limiting the sulfur content thereof.

DETAILED DESCRIPTION OF THE INVENTION

It is normal practice in all catalytic processes, particularly catalytic cracking processes, to, as nearly as possible, maintain a substantially constant temperature throughout the body of catalyst or reaction zone. Contrary to this general practice, it has been discovered, in accordance with the present invention, that $C_3$ and $C_4$ hydrocarbons can be converted to less saturated hydrocarbons, with improved selectivity to $C_2$ hydrocarbons and particularly ethylene, by maintaining a temperature differential between the upstream end of the body of catalyst and the downstream end of the body of catalyst and, specifically, by maintaining the temperature in the upstream end of the body of catalyst at least about 100° C. below the temperature in the downstream end of the body of catalyst.

In the art of utilizing solid contact materials, particularly catalysts, a wide variety of techniques have been developed for contacting normally liquid, vapor-phase and normally gaseous reactants with solid contact materials. For example, the reactants may be passed concurrently or countercurrently through a bed of catalyst, such as a fixed, moving, fluidized, ebullating or entrained bed of catalyst. However, in all of these techniques there is a confined or established body of catalyst with which the reactants are contacted. Accordingly, when the terms "establishing a body of catalyst", "body of catalyst" and the like are utilized in the present specification and the claims hereof, this terminology is meant to include a defined body of catalyst, usually an elongated body of catalyst, through which the reactants are passed from the upstream end of the body of catalyst to the downstream end of the body of catalyst and excludes any void space, essentially free of solid contact material, both upstream and downstream of the body of contact material. Thus, the body of catalyst can be established, in accordance with the present invention, by any of the known techniques for passing reactants through a body or bed of catalyst. Accordingly, in carrying out the present endothermic reaction, the entire body of catalyst is preheated, by means hereinafter mentioned, prior to contact with the reactants, in order to effectively utilize the catalyst for the purposes for which it is intended. However, in accordance with the present invention, the temperature in the upstream end of the body of catalyst (the end which is first contacted with the reactants) is maintained substantially below the temperature in the downstream end of the body of catalyst (the end from which products are withdrawn). Thus, the body of catalyst is further defined by an upstream end and a downstream end containing a sufficient volume of catalyst to be preheated and the temperature of which can be maintained at a predetermined level. When reference is made to the "midpoint" of the body of catalyst, this is the longitudinal midpoint with reference to the direction of flow of reactants through the body of catalyst.

The hydrocarbon feed, in accordance with the present invention, can include any normally gaseous hydrocarbon stream containing significant amounts of $C_3$ and $C_4$ hydrocarbons, particularly propane and n-butane, with n-butane being preferred. The presence of other normally gaseous components or even normally liquid components, which vaporize at operating conditions, are not detrimental to the process. For example, it has been found that, when isobutane is utilized, in accordance with the present invention, the catalysts of the present invention shift the product stream from isobutene to propylene and, therefore, one of the desired products of the present invention is produced. On the other hand, it has been found that the catalytic process of the present invention is ineffective, as compared with a strictly thermal process, in improving the conversion of ethane to ethylene. However, the presence of ethane in the feed hydrocarbons, obviously, is not determental. Components other than hydrocarbons are also not detrimental. The primary criteria in all cases is the cost or difficulty of separating inert materials or the products of components other than $C_3$ and $C_4$ hydrocarbons from the desired ethylene and propylene and whether such separation is less costly and/or less difficult before or after conduct of the process of the present invention. Suitable feedstocks for the process of the present invention can be obtained from any source, including natural gas, refinery off-gases and the like. However, the most convenient and abundant source is $C_3$ and $C_4$ hydrocarbon streams recovered during the processing of a natural gas to produce a pipeline gas for heating purposes. Conventionally, $C_2$ and higher hydrocarbons are separated from methane to produce a pipeline gas for heating purposes, which predominates in methane, by compression and expansion, cryogenic means or a combination of both. Usually, the natural gas, either at a high pressure as produced or compressed to a high pressure, is treated to successively condense first normally liquid hydrocarbons ($C_6+$ hydrocarbons or natural gasoline), then $C_5$, followed by $C_4$, then $C_3$ and finally, $C_2$ hydrocarbons, by cooling to successively lower temperatures with the separation or fractionation of the condensed liquid from uncondensed vapor between cooling stages. Thus, individual streams predominating in an individual hydrocarbon, such as $C_5$, $C_4$, $C_3$ and $C_2$, can be obtained or streams predominating in combinations of the individual hydrocarbons can be recovered. Accordingly, the thus separated propane stream or the thus separated butanes stream can be utilized as a feed hydrocarbon for the present invention or a stream predominating in a mixture of propane and butanes can be utilized. Obviously, the latter would eliminate the necessity of one stage of cooling and separation in a natural gas processing system.

Any of the known cracking catalysts, adapted to convert $C_3$ and $C_4$ hydrocarbons to less saturated hydrocarbons, are useful in accordance with the present invention. However, it is preferred, in accordance with the present invention, that a particular group of catalysts comprising mixed oxides of various metals be utilized, since these catalysts are highly effective for the conversion of $C_3$ and $C_4$ hydrocarbons to less saturated hydrocarbons, with a high selectivity to $C_2$ hydrocarbons and particularly ethylene, as opposed to propylene, and the active life of such catalysts, for the selective production of $C_2$ hydrocarbons and ethylene, before regeneration is desirable, is long as compared with conventional prior art catalysts. This group of catalysts includes:

(a) a catalyst comprising at least one oxide of manganese and at least one oxide of magnesium;

(b) a catalyst comprising at least one oxide of manganese and at least one oxide of at least one Lanthanum Series metal or niobium;

(c) a catalyst comprising at least one oxide of iron and at least one oxide of magnesium; and (d) a catalyst comprising at least one oxide of iron and at least one oxide of at least one Lanthanum series metal or niobium.

The effectiveness of these catalysts for the selective production of $C_2$ hydrocarbons and particularly ethylene, as opposed to propylene, and/or the active life of the catalyst for such selective production of $C_2$ hydrocarbons and ethylene, can be extended by the selective addition of certain metal oxide promoters. When the catalyst is a combination of oxides of manganese and magnesium, suitable promoters include calcium, strontium, barium, tin and/or antimony. This group of promoters has been found to have little or no effect or a detrimental effect on the remaining basic catalyst compositions. A second group of promoters includes oxides of silicon, aluminum and/or titanium. This group of promoters is useful on all of the catalysts containing an oxide of magnesium, but not on the catalysts containing oxides of Lanthanum Series metals or niobium. Finally, an oxide of chromium has been found to be an effective promoter for all of the above-mentioned catalysts. Further, in any of the catalysts containing an oxide of iron, an oxide of manganese may also be combined therewith as an active component.

It is also desirable to limit the amount of "bound" or "fixed" sulfur in the components used to prepare the catalysts of the present invention. It appears that the presence of such bound or fixed sulfur in the catalyst tends to inhibit the selectivity of the catalyst for the production of $C_2$ hydrocarbons. Such sulfur is referred to as "bound" or "fixed" sulfur, since it does not appear to be converted to hydrogen sulfide or to be otherwise lost during the hydrocarbon conversion process or the regeneration step and is probably present in sulfate form. Desirably, the sulfur content should be below about 0.2 wt. % expressed in terms of elemental sulfur based on the total weight of catalyst, and preferably below about 0.1 wt. %.

The exact compositions of the above catalysts are not fully understood, except to the extent that the components are predominantly in the form of oxides. Specifically, a particular cation may be pesent in the form of a single electrically balanced oxide, in the form of mixtures of several electrically balanced oxides or as mixtures of electrically balanced oxides and partial oxides. From time to time, herein, the oxides of magnesium, Lanthanum Series metals and niobium are referred to as base materials or base components, the oxides of manganese and iron as active components and the oxides of calcium, strontium, barium, tin, antimony, silicon, aluminum, titanium and chromium as promoters or promoting components. These references are utilized solely as a matter of convenience, based on the facts that the magnesium, Lanthanum Series metals and niobium components are preferably present in a major amount while the remaining components are present in minor amounts, the base components are ineffective alone and the manganese and iron components render the catalyst active and the oxides of calcium, strontium, barium, tin, antimony, silicon, aluminum, titanium and chromium further promote the activity of the catalysts and extend their active life. Accordingly, such references are not intended to categorize the components or the catalysts, since all components of a particular combination appear to be catalytically active in the process of the present invention.

In the preferred catalyst combinations, the oxides of magnesium, Lanthanum Series metals, preferably selected from the group consisting of lanthanum and cerium, and/or niobium are present in major amounts while the remaining oxides are present in minor amounts. The minor components or promoters or active components are preferably present in the mixtures in amounts between about 0.1 and about 30% by weight, expressed in terms of the element based on the total weight of the catalytic mixture. Ideally, the promoters or active components are present in amounts between about 0.5 and about 15% of the element based on the total weight of the mixture. Obviously, where combinations of promoters and/or active components are utilized in a given catalyst combination, the amounts of each will geneally be reduced.

The method of catalyst preparation does not appear to be critical, so long as the desired final composition of the component metal oxides is obtained. Suitable methods of preparation include slurry blending, solution blending, dry blending, impregnation and co-precipitation, all of which are well known to those skilled in the art. A convenient method is to add metal solids, such as MgO or $Mg(OH)_2$, to a blending apparatus along with an aqueous solution of a metal salt [for example $Mn(NO_3)_2$] and mixing for several minutes, for example, 2 to 15 minutes, to form a thick slurry. In the interest of economy, excess water should be avoided. Additional active components or promoters may also be added as desired, either as solids or solutions before or during blending. The resulting slurry is then dried in air by conventional means, at about 100° C. to 150° C., calcined for about four hours, at about 750° C. to 800° C., and then ground, sieved and, optionally, pelleted or otherwise sized by means well known in the art. The additional promoters and/or active components can also be added by impregnating the same on an oxide base or mixture of active oxide and base oxide formed by the above slurrying method.

As previously indicated, the process of the present invention can be carried out in fixed, moving, fluidized, ebulating or entrained bed reactors. For experimental purposes and, obviously, to permit accurate measurement and precise control of the process variables, the runs hereinafter set forth in the examples were conducted in a fixed bed reactor.

During operation, in accordance with the present invention, it has been found that small amounts of the feedstock are converted to coke, which is then deposited upon the catalyst and contributes to a decline in the catalyst activity, particularly the selectivity to ethylene. Accordingly, it is desirable to periodically regenerate the catalyst by conventional techniques of carbon removal, such as treatment with an oxygen-containing gas, such as air. During such regeneration, it may also be desirable to use inert gas or steam dilution to control burn-off temperatures, as is also well known to those skilled in the art.

In accordance with the present invention, the addition of steam to the feed hydrocarbon significantly extends the effective life of the catalyst between regenerations.

Following preparation of the catalyst, the catalyst may be prepared for use by purging with an inert gas, such as nitrogen. Normally, the catalyst would be disposed in the reactor and brought up to reaction temperature by preheating with air, then purging with hot nitrogen and, finally, introducing the hydrocarbon feed. Since it is preferred that steam be added to the hydrocarbon feed, in the conduct of the process of the present invention, it may be preferred to use steam rather than nitrogen as a purging gas. The catalyst may also, optionally, be pretreated with hydrogen before use. Such treatment is preferably carried out at about the operating temperature of the process and at a pressure up to about 600 psia. Such hydrogen pretreatment appears to reduce higher oxidation states of manganese and other multi-valent metals and reduce the initial formation of carbon oxides.

With the exception of the temperature of operation, the operating conditions of the process, in accordance with the present invention, do not appear to be highly critical. Accordingly, the following conditions of operation are those found effective and preferred.

The steam/hydrocarbon mole ratio may be between 0 and about 10/1, preferably about 0.1 to about 10/1 and is still more preferably about 0.5/1 to about 5/1.

The hydrocarbon gas hourly space velocity (GHSV) may range from about 100 to about 3000 but is preferably between about 500 and about 1000.

Operating pressure may be between about 0.1 and about 100 psia and is preferably between about 1 and about 60.

As previously indicated, control of the temperature of the body of catalyst is critical in obtaining the improved results of the present invention. The process of the present invention is most effective when the temperature at approximately the longitudinal midpoint of the body of catalyst is maintained between about 550° C. and 850° C. and preferably between about 650° C. and about 775° C. The operative and preferred temperatures in the downstream end of the body of catalyst will usually be about the same as the midpoint temperature but will be dictated to some extent by the temperature in the upstream end of the body of catalyst. However, three zone heaters or the like (which were utilized in the examples) can maintain different upstream, midpoint and downstream temperatures, if desired. In accordance with the present invention, the temperature in the upstream end of the body of catalyst is maintained at least 100° C. less than the temperature in the downstream end of the body of catalyst and preferably between about 100° C. and 200° C. below the temperature in the downstream end of the body of catalyst. Therefore, the temperature in the upstream end of the body of catalyst may be between about 400° C. and about 750° C., or preferably between about 550° C. and about 675° C.

The nature and advantages of the present invention are illustrated by the following example.

A 3% Ca/4% Mn/MgO catalyst was prepared by the slurrying method previously set forth. This catalyst was selected since other studies have established this to be one of the best catalysts for the selective conversion of $C_3$ and $C_4$ feed hydrocarbons to ethylene, from an overall standpoint. In the runs of the examples, the catalyst was placed in an 18 mm (i.d.) quartz reactor containing 25 cc of catalyst as a fixed bed. The catalyst bed had a total depth of approximately 10 cm.

Typically, the bed of catalyst was preheated by air oxidation for ten minutes, nitrogen purged for two minutes, hydrogen treated for ten minutes and, finally, nitrogen purged. The catalyst bed was brought up to the desired upstream and downstream temperatures before beginning the flow of feed hydrocarbons.

The feed hydrocarbon comprised n-butane at 100 cc/min and, additionally, steam was added at 100 cc/min. The feed and steam were simultaneously introduced at the top of the reaction column and products were withdrawn from the bottom of the reaction column.

Temperatures listed correspond to the temperature at approximately 1 cm from the top of the catalyst bed and approximately 3 cm from the bottom of the catalyst bed, representing the upstream end and downstream ends, respectively, of the catalyst bed. Snap samples of reactor effluent were analyzed by gas chromatography. Conversion is expressed as mole percent of n-butane converted and selectivities are based on the mole percent of n-butane converted to a particular product. In evaluating catalysts for the selective conversion to ethylene of $C_3$ and $C_4$ hydrocarbons, thermal, steam cracking was generally utilized as a basis of comparison. In such thermal cracking tests, quartz chips were substituted for the catalysts but otherwise the conditions and mode of operation were the same. Typically, when a bed temperature of about 700° C. was maintained throughout, the conversion of n-butane averages approximately 40%, the selectivity to ethylene is about 30%, the selectivity to propylene is about 40% and the selectivity to ethane is about 6% to 7%. Accordingly, the ratio of ethylene plus ethane to propylene is about 0.9 and the ratio of ethylene to propylene is about 0.75. Also, as a criteria for evaluating the effectiveness of the catalyst for the selective conversion to ethylene, as opposed to propylene, it was considered that when the selectivity to propylene approximately equaled the selectivity to ethylene, the catalyst was "ineffective" and desirably should be regenerated.

TABLE

| Temp °C. | | | | Selectivity | | | $C_2=+C_2$ | $C_2=$ |
|---|---|---|---|---|---|---|---|---|
| Top | Bottom | ΔT °C. | Conv. | $C_2=$ | $C_3=$ | $C_2$ | $C_3=$ | $C_3=$ |
| 635 | 619 | −16 | 30.8 | 32.2 | 28.6 | 23.4 | 1.94 | 1.13 |
| 660 | 643 | −17 | 39.6 | 32.4 | 29.3 | 20.3 | 1.80 | 1.11 |
| 676 | 659 | −17 | 47.8 | 32.0 | 28.8 | 18.4 | 1.75 | 1.11 |
| 701 | 686 | −15 | 61.7 | 30.7 | 29.7 | 13.5 | 1.48 | 1.04 |
| 720 | 707 | −13 | 72.3 | 31.3 | 28.6 | 11.2 | 1.49 | 1.09 |
| 599 | 691 | +92 | 31 | 36 | 26 | 24 | 2.31 | 1.39 |
| 631 | 726 | +95 | 50 | 37 | 28 | 22 | 2.11 | 1.32 |
| 645 | 740 | +95 | 57 | 37 | 25 | 19 | 2.24 | 1.48 |
| 662 | 759 | +97 | 67 | 37 | 26 | 16 | 2.04 | 1.42 |

It is to be observed from the first series of tests, represented by the first five runs, that when the temperature in the catalyst bed is maintained essentially constant throughout to produce a midpoint temperature approximately equal to the desired reaction temperature, as by heating the feed to a slightly higher temperature than the desired bed temperature and utilizing heating means about the catalyst bed, the temperature at the upstream end of the catalyst bed is generally about 15° C. above the temperature at the downstream end of the catalyst bed. Under these conditions of operation, it is to be seen that while the conversion of n-butane is high at a midpoint temperature of approximately 700° C., the ethylene/propylene ratio is approximately equal to a thermal cracking operation. However, the ethylene plus ethane/propylene ratio is substantially higher than that for a thermal cracking operation and, thus, the catalyst is effective at this temperature, since the ethane can be more readily converted to additional ethylene than other normally gaseous hydrocarbons. However, operating in accordance with the present invention, when the temperature in the upstream end of a catalyst bed was approximately 100° C. less than the temperature in the downstream end of the catalyst bed, the n-butane conversion was substantially the same as that obtained with an essentially constant bed temperature, but over the entire temperature range tested, the ratio of ethylene plus ethane/propylene was substantially increased by an average of about 40% and the ethylene to propylene ratio was substantially increased by an average of about 30%.

While specific materials, conditions of operation, modes of operation and equipment have been referred to herein, it is to be recognized that these and other specific recitals are for illustrative purposes and to set forth the best mode only and are not to be considered limiting.

We claim:

1. A method for converting feed hydrocarbons comprising at least one of $C_3$ and $C_4$ hydrocarbons to less saturated hydrocarbons, comprising:
    (a) establishing a body of cracking catalyst, in a reaction zone, selected from the group consisting essentially of:
        (1) a catalyst, consisting essentially of: about 0.1 to 30 wt. % of (A) at least one oxide of manganese and the balance of (B) at least one oxide of magnesium;
        (2) a catalyst, consisting essentially of: about 0.1 to 30 wt. % of (A) at least one oxide of at least one metal selected from the group consisting of calcium, strontium, barium, tin and antimony and (B) at least one oxide of manganese and the balance of (C) at least one oxide of magnesium;
        (3) a catalyst, consisting essentially of: about 0.1 to 30 wt. % of (A) at least one oxide of at least one metal selected from the group consisting of calcium, strontium, barium, tin and antimony, (B) at least one oxide of at least one element selected from the group consisting of silicon, aluminum and titanium and (C) at least one oxide of manganese and the balance of (D) at least one oxide of magnesium;
        (4) a catalyst, consisting essentially of: about 0.1 to 30 wt. % of (A) at least one oxide of at least one metal selected from the group consisting of calcium, strontium, barium, tin and antimony, (B) at least one oxide of chromium and (C) at least one oxide of manganese and the balance of (D) at least one oxide of magnesium;
        (5) a catalyst, consisting essentially of: about 0.1 to 30 wt. % of (A) at least one oxide of at least one element selected from the group consisting of silicon, aluminum and titanium and (B) at least one oxide of manganese and the balance of (C) at least one oxide of magnesium;
        (6) a catalyst, consisting essentially of: about 0.1 to 30 wt. % of (A) at least one oxide of chromium and (B) at least one oxide of manganese and the balance of (C) at least one oxide of magnesium;
        (7) a catalyst comprising: about 0.1 to 30 wt. % of (A) at least one oxide of manganese and the balance of (B) of at least one metal selected from the group consisting of Lanthanum Series metals and niobium; and
        (8) a catalyst comprising: about 0.1 to 30 wt. % of (A) at least one oxide of chromium and (B) at least one oxide of manganese and the balance of (C) at least one oxide of at least one metal selected from the group consisting of Lanthanum Series metals and niobium,
    said wt. % being expressed in terms of the element based on the total weight of catalyst,
    (b) introducing said feed hydrocarbons into the upstream end of said body of catalyst;
    (c) passing the thus introduced feed hydrocarbons through said body of catalyst and in contact therewith;
    (d) withdrawing said product hydrocarbons from the downstream end of said body of catalyst; and
    (e) maintaining conditions within said body of catalyst sufficient to convert said feed hydrocarbons to said product hydrocarbons, including: a temperature in said upstream end of said body of catalyst between about 400° C. and about 750° C. and a temperature at said downstream end of said body of catalyst between about 100° C. and about 200° C. above said temperature in said upstream end.

2. A method in accordance with claim 1 wherein the temperature in the downstream end of the catalyst bed is maintained between about 550° and 850° C.

3. A method in accordance with claim 1 wherein the catalyst consists essentially of (A) at least one oxide of at least one metal selected from the group consisting of calcium, strontium, barium, tin and antimony, (B) at least one oxide of manganese and (C) at least one oxide of magnesium.

4. A method in accordance with claim 1 wherein the catalyst consists essentially of (A) at least one oxide of at least one metal selected from the group consisting of calcium, strontium, barium, tin and antimony, (B) at least one oxide of at least one element selected from the group consisting of silicon, aluminum and titanium, (C) at least one oxide of manganese and (D) at least one oxide of magnesium.

5. A method in accordance with claim 1 wherein the catalyst consists of (A) at least one oxide of at least one metal selected from the group consisting of calcium, strontium, barium, tin and antimony, (B) at least one oxide of chromium, (C) at least one oxide of manganese and (D) at least one oxide of magnesium.

6. A method in accordance with 1 wherein the catalyst consists essentially of (A) at least one oxide of at least one element selected from the group consisting of silicon, aluminum and titanium, (B) at least one oxide of manganese and (C) at least one oxide of magnesium.

7. A method in accordance with claim 1 wherein the catalyst consists essentially of (A) at least one oxide of chromium, (B) at least one oxide of manganese and (C) at least one oxide of magnesium.

8. A method in accordance with claim 1 wherein the catalyst comprises (A) at least one oxide of manganese and (B) at least one oxide of at least one metal selected from the group consisting of Lanthanum Series in niobium.

9. A method in accordance with claim 1, wherein the catalyst comprises (A) at least one oxide of chromium, (B) at least one oxide of manganese and (C) at least one oxide of at least one metal selected from the group consisting of Lanthanum Series metals and niobium.

10. A method in accordance with claim 1 wherein the temperature at about the longitudinal midpoint of the body of catalyst is maintained between about 550° and about 850° C.

11. A method in accordance with claim 1 wherein the catalyst comprises at least one oxide of manganese and at least one oxide of magnesium.

12. A method in accordance with claim 1 wherein the catalyst comprises at least one oxide of manganese and at least one oxide of at least one metal selected from the group consisting of Lanthanum Series metals and niobium.

13. A method in accordance with claim 12 wherein the metal selected from the group consisting of Lanthanum Series metals is a metal selected from the group consisting of lanthanum and cerium.

14. A method in accordance with claim 1 wherein the feed hydrocarbons are contacted with the catalyst in the presence of steam.

15. A method in accordance with claim 14 wherein the mole ratio of steam/feed hydrocarbons is between about 0.1/1 and about 10/1.

16. A method in accordance with claim 1 wherein the feed hydrocarbons comprise propane.

17. A method in accordance with claim 1 wherein the feed hydrocarbons comprise butanes.

18. A method in accordance with claim 1 wherein the feed hydrocarbons comprise a mixture of propane and butanes.

19. A method in accordance with claim 1 wherein the conditions are sufficient to selectively convert the feed hydrocarbons to $C_2$ hydrocarbons.

20. A method in accordance with claim 19 wherein the conditions are sufficient to selectively convert the feed hydrocarbons to ethylene.

21. A method for converting feed hydrocarbons comprising at least one of $C_3$ and $C_4$ hydrocarbons to less saturated hydrocarbons, comprising:
 (a) establishing a body of a cracking catalyst, in a reaction zone, selected from the group consisting of:
  (1) a catalyst, consisting essentially of: about 0.1 to 30 wt. % of (A) at least one oxide of iron and the balance of (B) at least one oxide of magnesium;
  (2) a catalyst, consisting essentially of: about 0.1 to 30 wt. % of (A) at least one oxide of iron and (B) at least one oxide of maganese and the balance of (C) at least one oxide of magnesium;
  (3) a catalyst, consisting essentially of: about 0.1 to 30 wt. % of (A) at least one oxide of iron, (B) at least one oxide of manganese and (C) at least one oxide of at least one element selected from the group consisting of silicon, aluminum and titanium and the balance of at least one oxide of magnesium;
  (4) a catalyst, consisting essentially of: about 0.1 to 30 wt. % of (A) at least one oxide of iron, (B) at least one oxide of manganese and (C) at least one oxide of chromium and the balance of (D) at least one oxide of magnesium;
  (5) a catalyst, consisting essentially of: about 0.1 to 30 wt. % of (A) at least one oxide of iron and (B) at least one oxide of at least one metal selected from the group consisting of silicon, aluminum and titanium and the balance of (C) at least one oxide of magnesium;
  (6) a catalyst, consisting essentially of: about 0.1 to 30 wt. % of (A) at least one oxide of iron and (B) at least one oxide of chromium and the balance of (C) at least one oxide of magnesium;
  (7) a catalyst, comprisng: about 0.1 to 30 wt. % of (A) at least one oxide of iron and the balance of (B) at least one oxide of at least one metal selected from the group consisting of Lanthanum Series metals and niobium;
  (8) a catalyst, comprising: about 0.1 to 30 wt. % of (A) at least one oxide of iron and (B) at least one oxide of manganese and the balance of (C) at least one oxide of at least one metal selected from the group consisting of Lanthanum Series metals and niobium;
  (9) a catalyst, comprising: about 0.1 to 30 wt. % of (A) at least one oxide of iron, (B) at least one oxide of manganese and (C) at least one oxide of chromium and the balance of (D) at least one oxide of at least one metal selected from the group consisting of Lanthanum Series metals and niobium; and
  (10) a catalyst comprising: about 0.1 to 30 wt. % of (A) at least one oxide of iron and (B) at least one oxide of chromium and the balance of (C) at least one oxide of at least one metal selected from the group consisting of Lanthanum Series metals and niobium,
 said wt. % being expressed in terms of the element based on the total weight of the catalyst,
 (b) introducing said feed hydrocarbons and steam into the upstream end of said body of catalyst;
 (c) passing said feed hydrocarbons and steam through said body of catalyst and in contact therewith;
 (d) withdrawing said product hydrocarbons from the downstream end of said body of catalyst; and
 (e) maintaining conditions within said body of catalyst sufficient to convert said feed hydrocarbons to said product hydrocarbons, including: a temperature in said upstream end of said body of catalyst between about 400° C. and about 750° C. and a temperature in said downstream end of said body of catalyst between about 100° C. and 200° C. above said temperature in said upstream end.

22. A method in accordance with claim 21 wherein the temperature at about the longitudinal midpoint of the body of catalyst is maintained between about 550° C. and about 850° C.

23. A method in accordance with claim 21 wherein the temperature in the downstream end of the body of catalyst is maintained between about 550° C. and about 850° C.

24. A method in accordance with claim 21 wherein the catalyst consists essentially of (A) at least one oxide of iron, (B) at least one oxide of manganese and (C) at least one oxide of magnesium.

25. A method in accordance with claim 21 wherein the catalyst consists essentially of (A) at least one oxide of iron, (B) at least one oxide of manganese, (C) at least one oxide of at least one element selected from the group consisting of silicon, aluminum and titanium and (D) at least one oxide of magnesium.

26. A method in accordance with claim 21 wherein the catalyst consists essentially of (A) at least one oxide of iron, (B) at least one oxide of manganese, (C) at least one oxide of chromium and (D) at least one oxide of magnesium.

27. A method in accordance with claim 21 wherein the catalyst consists essentially of (A) at least one oxide of iron, (B) at least one oxide of at least one metal selected from the group consisting of silicon, aluminum and titanium and (C) at least one oxide of magnesium.

28. A method in accordance with claim 21 wherein the catalyst consists essentially of (A) at least one oxide of iron, (B) at least one oxide of chromium and (C) at least one oxide of magnesium.

29. A method in accordance with claim 21 wherein the catalyst consists essentially of at least one oxide of iron and at least one oxide of magnesium.

30. A method in accordance with claim 21 wherein the catalyst comprises at least one oxide of iron and at least one oxide of at least one metal selected from the group consisting of Lanthanum Series metals and niobium.

31. A method in accordance with claim 30 wherein the metal selected from the group consisting of Lanthanum Series metals is a metal selected fromd the group consisting of lanthanum and cerium.

32. A method in accordance with claim 21 wherein the catalyst comprises (A) at least one oxide of iron, (B) at least one oxide of manganese and (C) at least one oxide of at least one metal selected from the group consisting of Lanthanum Series metals and niobium.

33. A method in accordance with claim 21 wherein the catalyst comprises (A) at least one oxide of iron, (B) at least one oxide of manganese, (C) at least one oxide of chromium and (D) at least one oxide of at least one metal selected from the group consisting of Lanthanum Series metals and niobium.

34. A method in accordance with claim 21 wherein the catalyst comprises (A) at least one oxide of iron, (B) at least one oxide of chromium and (C) at least one oxide of at least one metal selected from the group consisting of Lanthanum Series metals and niobium.

35. A method in accordance with claim 21 wherein the mole ratio of steam/feed hydrocarbons is between about 0.1/1 and about 10/1.

36. A method in accordance with claim 21 wherein the feed hydrocarbons comprise propane.

37. A method in accordance with claim 21 wherein the feed hydrocarbons comprise butanes.

38. A method in accordance with claim 21 wherein the feed hydrocarbons comprise a mixture of propane and butanes.

39. A method in accordance with claim 21 wherein the conditions are sufficient to selectively convert the feed hydrocarbons to $C_2$ hydrocarbons.

40. A method in accordance with claim 21 wherein the conditions are sufficient to selectively convert the feed hydrocarbons to ethylene.

* * * * *